(12) United States Patent
Xue et al.

(10) Patent No.: US 6,268,379 B1
(45) Date of Patent: Jul. 31, 2001

(54) SUBSTITUTED ARYL HYDROXAMIC ACIDS AS METALLOPROTEINASE INHIBITORS

(75) Inventors: Chu-Biao Xue, Hockessin; Carl P. Decicco, Newark; Ruth R. Wexler, Wilmington, all of DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/311,168

(22) Filed: May 13, 1999

Related U.S. Application Data
(60) Provisional application No. 60/085,393, filed on May 14, 1998.

(51) Int. Cl.[7] ............... C07D 217/00; C07D 213/02; A61K 31/44; A61K 31/47
(52) U.S. Cl. ............ 514/307; 514/311; 514/357; 546/139; 546/148; 546/152; 546/337
(58) Field of Search ................. 546/139, 148, 546/152, 337; 514/307, 311, 357

(56) References Cited

FOREIGN PATENT DOCUMENTS

| | | |
|---|---|---|
| 0780386 | 6/1997 | (EP) . |
| 9600214 | 1/1996 | (WO) . |
| 9839315 | 9/1998 | (WO) . |

Primary Examiner—Zinna Northington Davis

(57) ABSTRACT

The present application describes novel substituted aryl hydroxamic acids of formula I:

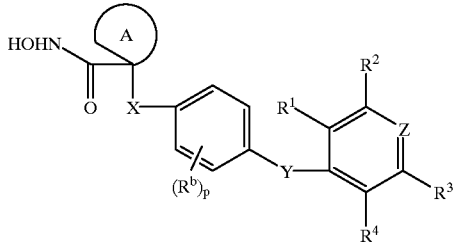

or pharmaceutically acceptable salt forms thereof, wherein ring A is a 5–8 membered ring containing from 0–2 heteroatoms selected from N, 0, and S, which are useful as metalloprotease inhibitors.

28 Claims, No Drawings

SUBSTITUTED ARYL HYDROXAMIC ACIDS AS METALLOPROTEINASE INHIBITORS

This application claims the benefit of U.S. Provisional Application No. 60/085,393 filed May 14, 1998.

FIELD OF THE INVENTION

This invention relates generally to novel substituted aryl hydroxamic acid derivatives as metalloproteinase inhibitors, and inhibitors of TNF, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. In addition metalloproteinases have been shown to be involved in the processing of cell surface proteins that have been implicated in a number of diseases, including inflammatory disorders.

Tumor necrosis factor alpha (TNF-α) is a cell associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF-α are therefore of therapeutic importance for the treatment of inflammatory disorders. Recently it has been shown that a matrix metalloproteinase (MMP) or family of metalloproteinases, hereafter known as TNF-convertases (TNF-C), as well as other MP's are capable of cleaving TNF-α from its cell associated to soluble form (Gearing et al Nature, 1994, 370, 555). This invention describes molecules that inhibit this conversion and hence the secretion of active TNF-α a from cells.

The compounds of the current invention inhibit the production of TNF-α from cells stimulated with LPS. Furthermore, some of the present compounds are selective for TNF-C inhibition over matrix metalloproteinases. This selectivity offers a distinct advancement over compounds of the current art, because non-selective MMP inhibitors have been found to produce toxic manifestations related to tendonitis and fibroplasia in clinical trials.

The compounds of the current invention do not inhibit MMPs at concentrations expected to produce a therapeutically positive response through the inhibition of TNF. The compounds of the present invention are therefore expected to be safer to patients taking the drug because of their selective inhibition profile for soluble TNF-α production.

The present novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV, neuro-denerative diseases and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechansisms are involved.

EP 0,780,386 describes MMP inhibitors of formula A:

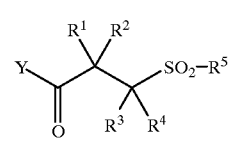

wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl. EP 0,780,386 does not disclose any compounds wherein Ar is a disubstituted phenyl or pyridyl or a bicyclic heteroaryl group.

The compounds of the current invention act as inhibitors of MPs, that process TNF-α. These novel molecules are provided as anti-inflammatory compounds and cartilage protecting therapeutics. The inhibiton of TNF-C, and other metalloproteinases by molecules of the present invention indicates they are anti-inflammatory.

SUMMARY OF THE INVENTION

Accordingly, one object of the present invention is to provide novel substituted aryl hydroxamic acids which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors, discovery that compounds of formula (I):

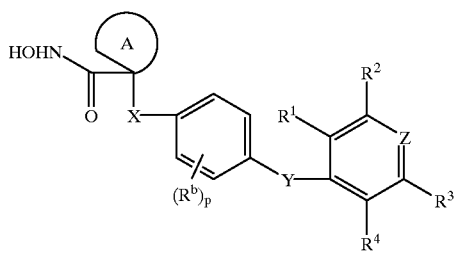

or pharmaceutically acceptable salt or prodrug forms thereof, wherein A, p, X, Y, Z, $R^b$, $R^1$, $R^2$, $R^3$, and $R^4$ are defined below, are effective metalloprotease inhibitors with unique and specific inhibitory properties for TNF.

DETAILED DESCRIPTION OF PREFERRED EMBODIMENTS

[1] Thus, in a first embodiment, the present invention provides a novel compound of formula I:

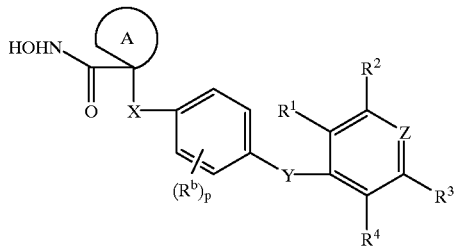

or a stereoisomer or pharmaceutically acceptable salt form thereof, wherein;

ring A is a 5–8 membered cyclic system containing 0–2 heteroatoms selected from the group: O, NH, S, SO, and $SO_2$, and substituted with 0–3 $R^a$;

$R^a$, at each occurrence, is independently selected from the group: =O, $CH_3$, $CH_2CH_3$, $CF_3$, Cl, F, OH, $OCH_3$, and $OCF_3$;

$R^b$, at each occurrence, is independently F or $CH_3$;

X is selected from the group: $CH_2C(O)$, $CH_2C(O)O$, $CH_2C(O)NH$, $CH_2S(O)$, $CH_2S(O)_2$, $CH_2S(O)NH$, and $CH_2S(O)_2NH$;

Y is selected from the group: $OCH_2$, $CH_2O$, $OCH(CH_3)$, $CH(CH_3)O$, $OC(CH_3)_2$, $C(CH_3)_2O$, $OCF_2$, $CF_2O$, $S(O)_pCH_2$, $CH_2S(O)_p$, $NHCH_2$, and $CH_2NH$;

Z is CH or N;

$R^1$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^2$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^3$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

provided that when Z is N, $R^2$ and $R^3$ are other than F, Br, or I;

$R^4$ is H;

alternatively, $R^3$ and $R^4$ are taken together with the carbon atoms to which they are attached to form a 5–6 membered aromatic ring containing 0–2 heteroatoms selected from the group: O, S, NH, and N and substituted with 0–2 $R^c$;

$R^c$ is selected from the group: H, F, Cl, Br, I, $NO_2$, $CH_3$, $CH_2CH_3$, $CH(CH_3)_2$, $OCH_3$, $OCH_2CH_3$, $OCH(CH_3)_2$, $CF_3$, and $OCF_3$;

when $R^3$ and $R^4$ are taken together, then $R^2$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

n is selected from the group: 1, 2, and 3; and, p is selected from the group: 0, 1, and 2.

[2] In a preferred embodiment, the present invention provides compound of formula Ia:

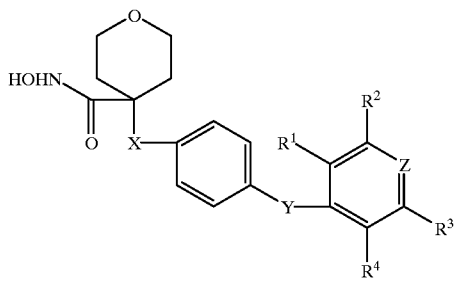

wherein, X is selected from the group: $CH_2$, C(O), C(O)O, C(O)NH, S(O), $S(O)_2$, S(O)NH, and $S(O)_2NH$;

Y is selected from the group: $(CH_2)_2$, $OCH_2$, $CH_2O$, $NHCH_2$, and $CH_2NH$;

Z is CH or N;

$R^1$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^2$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^3$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^4$ is H;

alternatively, $R^3$ and $R^4$ are taken together with the aromatic ring to which they are attached to form an aromatic ring selected from a–aa:

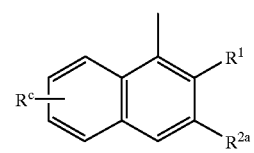

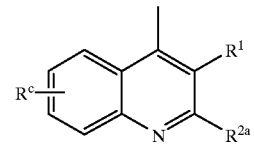

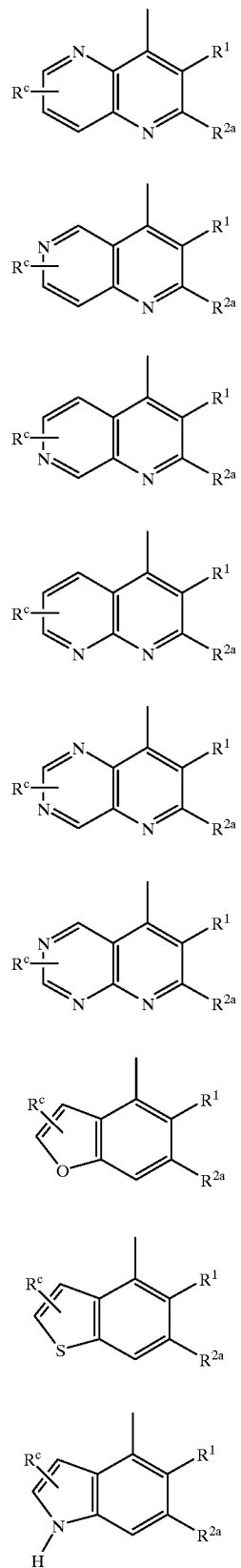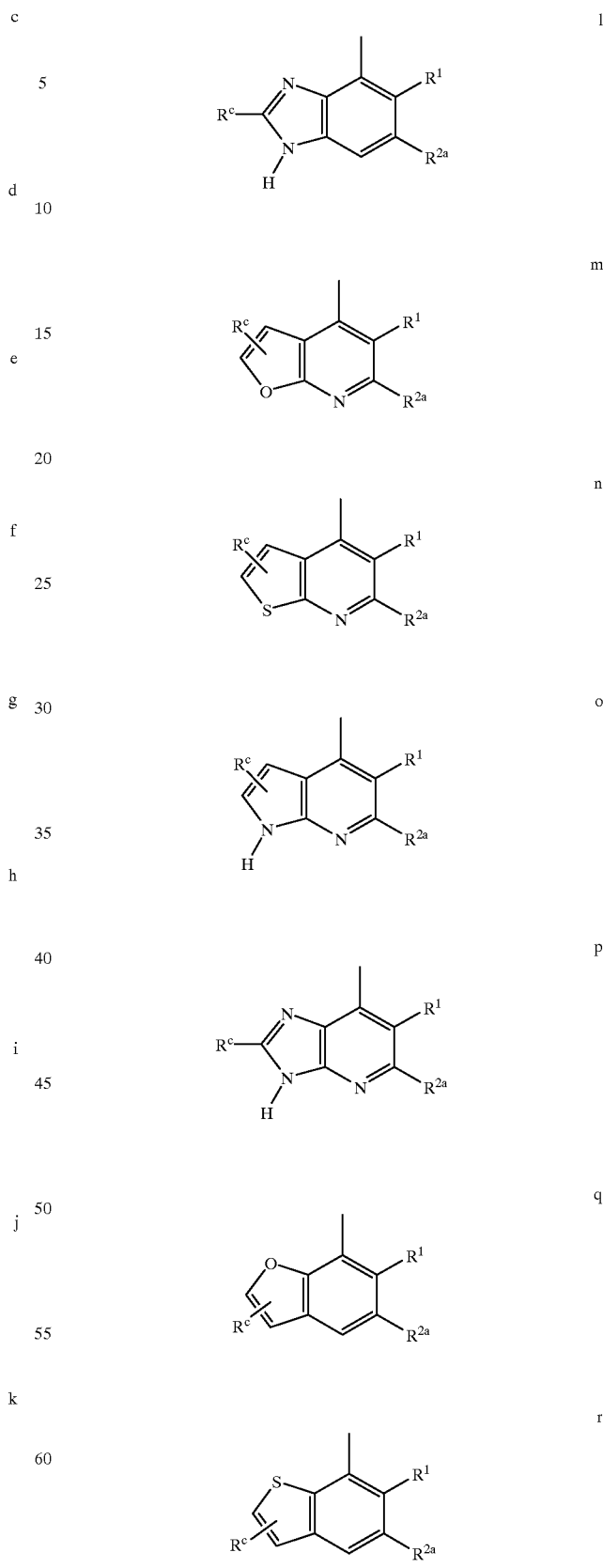

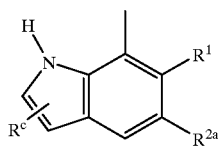
r
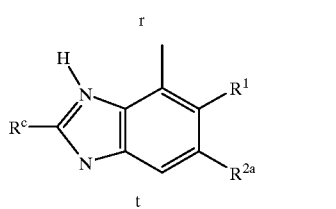
t
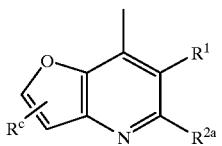
u
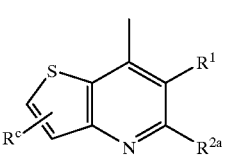
v
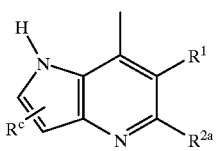
w
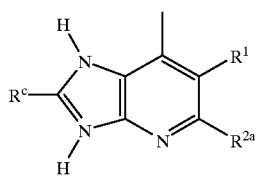
x
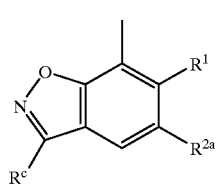
y
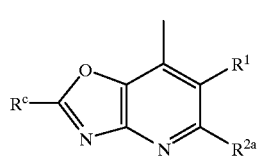
z s
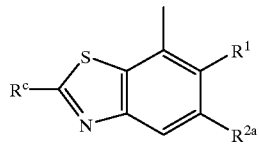
aa $R^c$ is selected from the group: H, F, Cl, Br, I, NO$_2$, CH$_3$, CH$_2$CH$_3$, CH(CH$_3$)$_2$, OCH$_3$, OCH$_2$CH$_3$, OCH(CH$_3$)$_2$, CF$_3$, and OCF$_3$; and, $R^{2a}$ is selected from the group: H, F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$.

[3] In a more preferred embodiment, the present invention provides a compound selected from:

4-[[[4-[(2,6-dimethyl-4-pyridinyl)methoxy]phenyl]sulfonyl]methyl]-tetrahydro-N-hydroxy-2H-pyran-4-carboxamide;
Tetrahydro-N-hydroxy-4-[[[4-(4-quinolinylmethoxy)phenyl]sulfonyl]methyl]-2H-pyran-4-carboxamide;
Tetrahydro-N-hydroxy-4-[[[4-(5-quinolinylmethoxy)phenyl]sulfonyl]methyl]-2H-pyran-4-carboxamide;
Tetrahydro-N-hydroxy-4-[[[4-(5-isoquinolinylmethoxy)phenyl]sulfonyl]methyl]-2H-pyran-4-carboxamide;
$N^4$-Hydroxy-4-[[[4-(4-quinolinylmethoxy)phenyl]sulfonyl]methyl]-4-piperidinecarboxamide;
$N^4$-Hydroxy-4-[[[4-(5-quinolinylmethoxy)phenyl]sulfonyl]methyl]-4-piperidinecarboxamide;
$N^4$-Hydroxy-4-[[[4-(5-isoquinolinylmethoxy)phenyl]sulfonyl]methyl]-4-piperidinecarboxamide;
1-Methanesulfonyl-4-[[[4-(4-quinolinylmethoxy)phenyl]sulfonyl]methyl]-N-hydroxy-4-piperidinecarboxamide;
1-Methanesulfonyl-4-[[[4-(5-quinolinylmethoxy)phenyl]sulfonyl]methyl]-N-hydroxy-4-piperidinecarboxamide;
11-Methanesulfonyl-4-[[[4-(5-isoquinolinylmethoxy)phenyl]sulfonyl]methyl]-N-hydroxy-4-piperidinecarboxamide;
11-Methoxycarbonyl-4-[[[4-(4-quinolinylmethoxy)phenyl]sulfonyl]methyl]-N-hydroxy-4-piperidinecarboxamide;
11-Methoxycarbonyl-4-[[[4-(5-quinolinylmethoxy)phenyl]sulfonyl]methyl]-N-hydroxy-4-piperidinecarboxamide;
11-Methoxycarbonyl-4-[[[4-(5-isoquinolinylmethoxy)phenyl]sulfonyl]methyl]-N-hydroxy-4-piperidinecarboxamide;
11-Cyclopropanecarbonyl-4-[[[4-(4-quinolinylmethoxy)phenyl]sulfonyl]methyl]-N-hydroxy-4-piperidinecarboxamide;
11-Cyclopropanecarbonyl-4-[[[4-(5-quinolinylmethoxy)phenyl]sulfonyl]methyl]-N-hydroxy-4-piperidinecarboxamide;
11-Cyclopropanecarbonyl-4-[[[4-(5-isoquinolinylmethoxy)phenyl]sulfonyl]methyl]-N-hydroxy-4-piperidinecarboxamide;
11-Cyclopropyl-4-[[[4-(4-quinolinylmethoxy)phenyl]sulfonyl]methyl]-N-hydroxy-4-piperidinecarboxamide;
11-Cyclopropyl-4-[[[4-(5-quinolinylmethoxy)phenyl]sulfonyl]methyl]-N-hydroxy-4-piperidinecarboxamide; and,
11-Cyclopropyl-4-[[[4-(5-isoquinolinylmethoxy)phenyl]sulfonyl]methyl]-N-hydroxy-4-piperidinecarboxamide;
or a pharmaceutically acceptable salt form thereof.

[4] In a second embodiment, the present invention provides a novel compound of formula II:

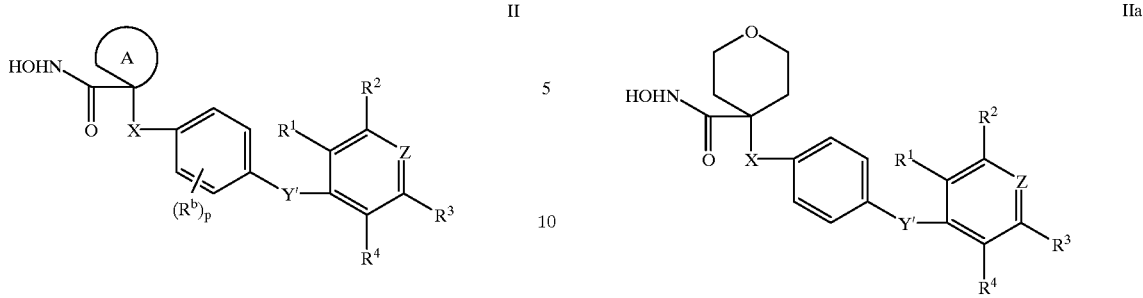

or a stereoisomer or pharmaceutically acceptable salt form thereof, wherein;

- ring A is a 5–8 membered cyclic system containing 0–2 heteroatoms selected from the group: O, NH, S, SO, and SO$_2$, and substituted with 0–3 R$^a$;
- R$^a$, at each occurrence, is independently selected from the group: =O, CH$_3$, CH$_2$CH$_3$, CF$_3$, Cl, F, OH, OCH$_3$, and OCF$_3$;
- R$^b$, at each occurrence, is independently F or CH$_3$;
- X is selected from the group: CH$_2$C(O), CH$_2$C(O)O, CH$_2$C(O)NH, CH$_2$S(O), CH$_2$S(O)$_2$, CH$_2$S(O)NH, and CH$_2$S(O)$_2$NH;
- Y' is selected from the group: CH$_2$, O, and NH;
- Z is CH or N;
- R$^1$ is selected from the group: H, F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- R$^2$ is selected from the group: F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- R$^3$ is selected from the group: H, F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- provided that when Z is N, R$^2$ and R$^3$ are other than F, Br, or I;
- R$^4$ is H;
- alternatively, R$^3$ and R$^4$ are taken together with the carbon atoms to which they are attached to form a 5–6 membered aromatic ring containing 0–2 heteroatoms selected from the group: O S, NH, and N and substituted with 0–1 R$^c$;
- R$^c$ is selected from the group: H, F, Cl, Br, I, NO$_2$, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- when R$^3$ and R$^4$ are taken together, then R$^2$ is selected from the group: H, F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- n is selected from 1, 2, and 3; and,
- p is selected from 0, 1, and 2.

[5] In a preferred embodiment, the present invention provides a compound of formula IIa:

wherein, X is selected from the group: CH$_2$, C(O), C(O)O, C(O)NH, S(O), S(O)$_2$, S(O)NH, and S(O)$_2$NH;

- Y is selected from the group: CH$_2$, O, S, and NH;
- Z is CH or N;
- R$^1$ is H or F;
- R$^2$ is selected from the group: F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- R$^3$ is selected from the group: F, Cl, Br, I, CH$_3$, CH$_2$CH$_3$, CH(CH$_3$)$_2$, OCH$_3$, OCH$_2$CH$_3$, OCH(CH$_3$)$_2$, CF$_3$, and OCF$_3$;
- R$^4$ is H;
- alternatively, R$^3$ and R$^4$ are taken together with the aromatic ring to which they are attached to form an aromatic ring selected from a–aa:

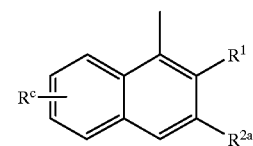

a

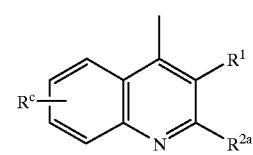

b

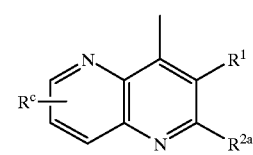

c

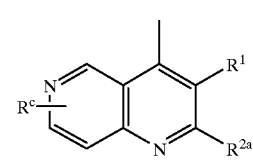

d

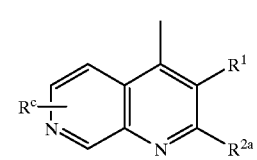

e f
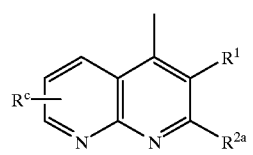
g
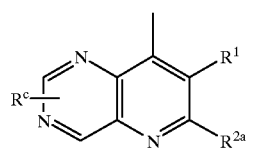
h
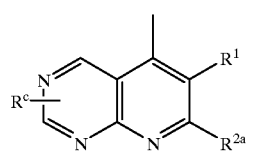
i
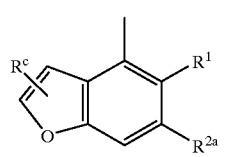
j
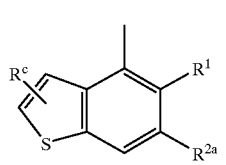
k
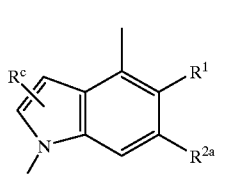
l
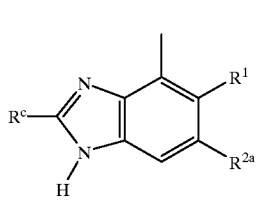
m
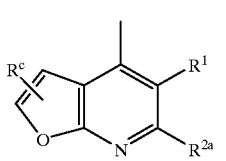
n
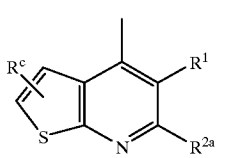
o
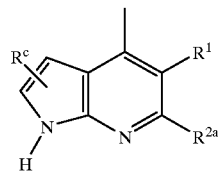
p
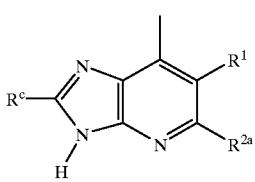
q
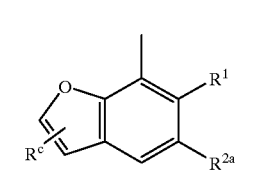
r
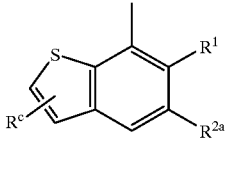
s
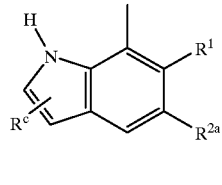
t
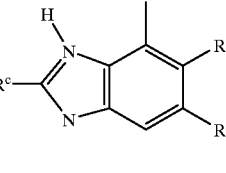
u
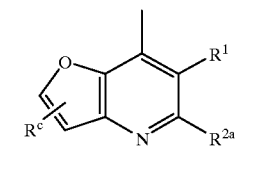
v
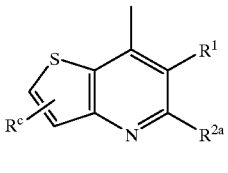
w
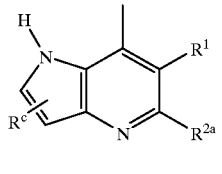

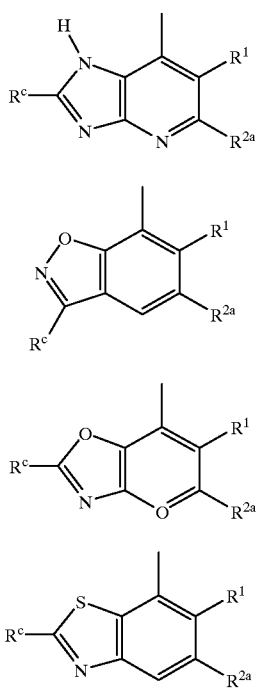

$R^c$ is selected from the group: H, F, Cl, Br, I, $NO_2$, $CH_3$, $CH_2CH_3$, $CH(CH_3)_2$, $OCH_3$, $OCH_2CH_3$, $OCH(CH_3)_2$, $CF_3$, and $OCF_3$; and, $R^{2a}$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$.

In a third embodiment, the present invention provides a novel pharmaceutical composition, comprising: a pharmaceutically acceptable carrier and a therapeutically effective amount of a compound of formula (I) or (II) or a pharmaceutically acceptable salt form thereof.

In a fourth embodiment, the present invention provides a novel method for treating or preventing an inflammatory disorder, comprising: administering to a patient in need thereof a therapeutically effective amount of a compound of formula (I) or (II) or a pharmaceutically acceptable salt form thereof.

In a fifth embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula (I) or (II) or a pharmaceutically acceptable salt form thereof.

In a sixth embodiment, the present invention provides a novel method of reducing levels of TNF in patients without inhibiting MMPs, comprising: MMP-1, MMP-2, and MMP-9, and reduce the potential of side effects mediated by these enzymes comprising: administering to the mammal in need of such treatment a therapeutically effective amount of a compound of formula (I) or (II) or a pharmaceutically acceptable salt form thereof.

In a seventh embodiment, the present invention provides a novel method of treating a condition or disease wherein the disease or condition is referred to as rheumatoid arthritis, osteoarthritis, periodontitis, gingivitis, corneal ulceration, multiple sclerosis, neurodegenerative diseases, psoriasis, autoimmune disease, Crohn's disease, inflammatory bowel disease, or HIV infection in a mammal, comprising: administering to the mammal in need of such treatment a therapeutically effective amount of a compound of formula (I) or (II) or a pharmaceutically acceptable salt form thereof.

In a eighth embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, solid tumor growth and tumor invasion by secondary metastases, or neovascular glaucoma, in a mammal comprising administering to the mammal in need of such treatment a therapeutically effective amount of a compound of formula (I) or (II) or a pharmaceutically acceptable salt form thereof.

A ninth embodiment of the invention provides novel preferred compounds that are orally bioavailable and selective for the inhibition of TNF-α through its convertase(s), over enzymes of the matrix metalloproteinase class.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" or "$C_{1-6}$ alkylene" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" or "alkenylene" is intended to include hydrocarbon chains of either a straight or branched configuration and one or more unsaturated carbon-carbon bonds which may occur in any stable point along the chain, such as ethenyl, propenyl, and the like. "Alkynyl" or "alkynylene" is intended to include hydrocarbon chains of either a straight or branched configuration and one or more carbon-carbon triple bonds which may occur in any stable point along the chain, such as ethynyl, propynyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 8-membered monocyclic or bicyclic or 7- to 14-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 14-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula I where A is a tetrahydropyran, piperidine, or 3,4,5,6-tetrahydro-2(1H)-pyrimidinone, X is $CH_2SO_2$ and Y is $OCH_2$ or $NHCH_2$ can be prepared using the methods outlined in Schemes 1–6. The synthesis of the tetrahydropyran derivative 14 can follow the procedures described previously (S. L. Bender et al. EP 0,780,386 A1). The piperidine ring and the 3,4,5,6-tetrahydro-2(1H)-pyrimidinone ring can be constructed using the procedures described in Scheme 1 and Scheme 2, respectively. The synthesis of the piperidine derivative 5 can start from ethyl 4-piperidinecarboxylate 1. Derivatization at the nitrogen with a chloroformate, a sulfonyl chloride or an aldehyde should produce the intermediate 2. An aldol reaction of 2 with paraformaldehyde using LDA can give the quaternary carboxylate 3 which may be hydrolyzed to afford acid 4. The β-lactone 5 may then be generated via ring closure of 4 by treating 4 with benzenesulfonyl chloride.

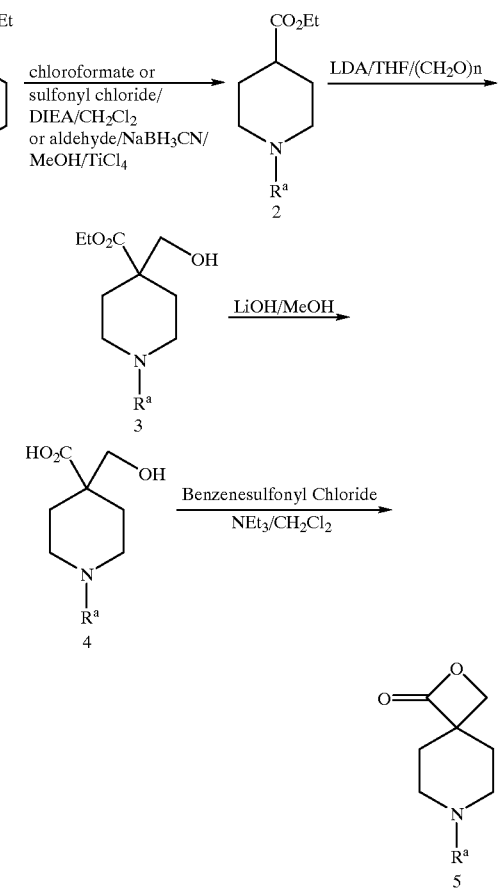

The synthesis of 3,4,5,6-tetrahydro-2(1H)-pyrimidinone derivative 13 can start from methyl cyanoacetate 6 which is alkylated with cyanogen bromide to give the bis-cyanoacetate 7. Hydrogenation should convert the nitrile to the amine 8. Reaction of 8 with 1,1'-carbonyldiimidazole can then lead to formation of a 3,4,5,6-tetrahydro-2(1H)-pyrimidinone ring 9. Alkylation at both nitrogens with a halide or a sulfonate can give the alkylated product 10 which is then subjected to an aldol reaction to give 11. The methyl ester can then be saponified and the resulting acid may then be treated with benzenesulfonyl chloride to give the β-lactone 13.

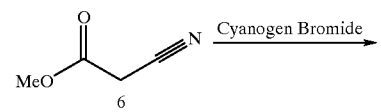

-continued

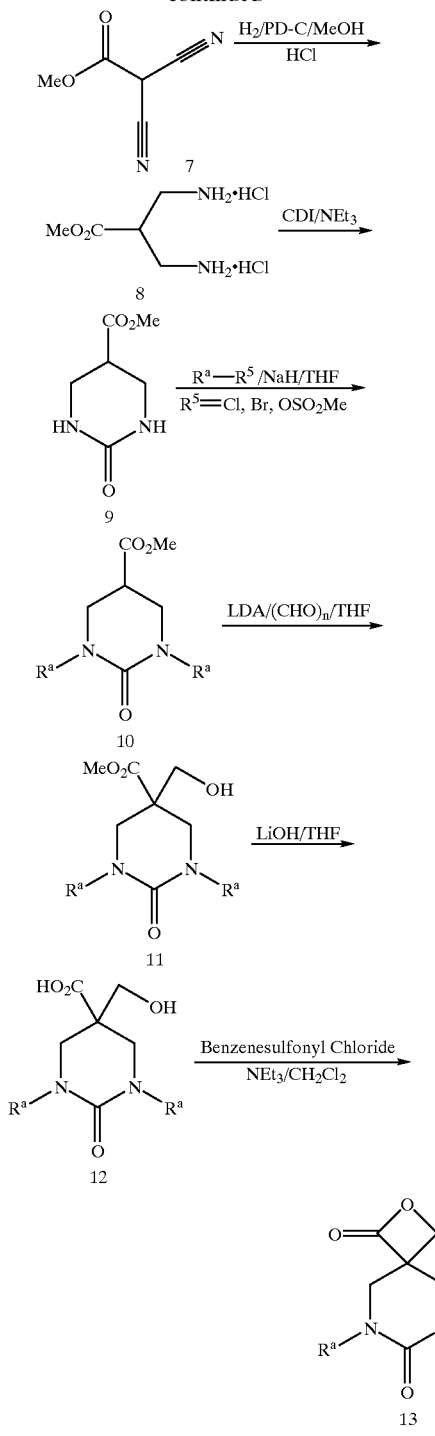

Scheme 3

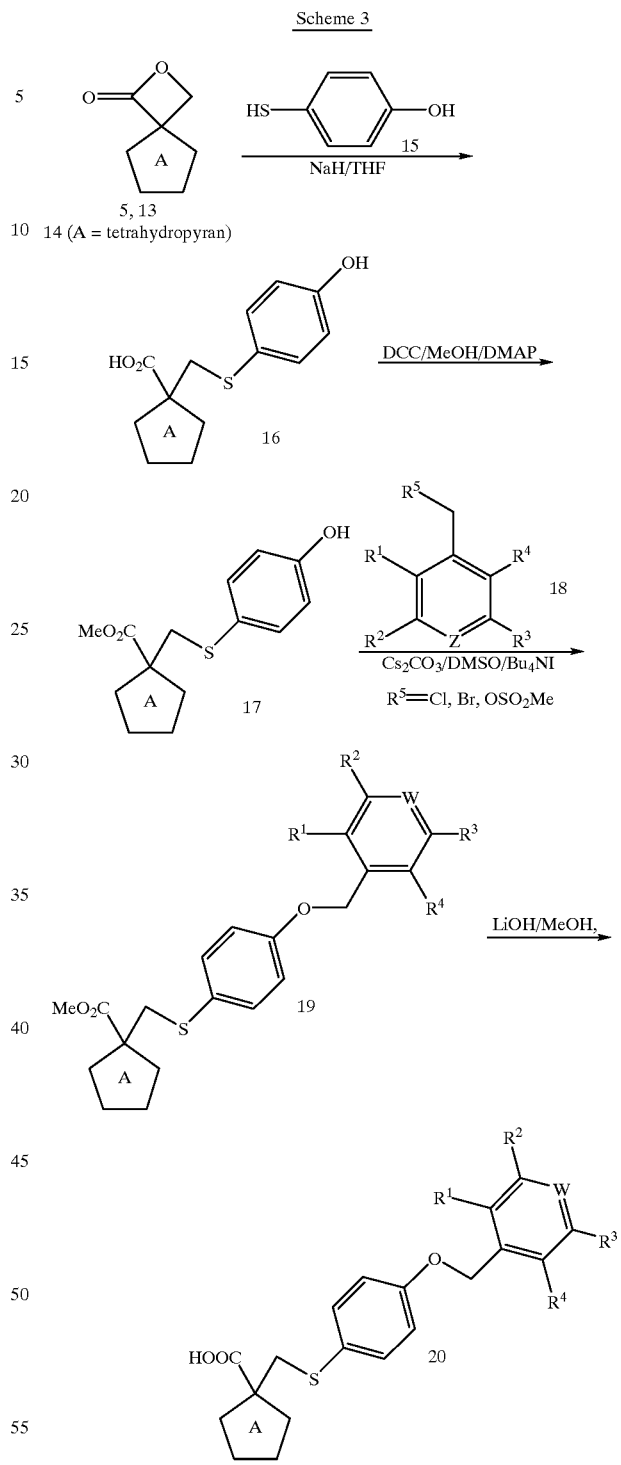

The lactone derivatives 5, 13 and 14 can be converted to a phenylether intermediate 20 using either the method shown in Scheme 3 or that shown in Scheme 4. Ring opening of 5, 13 or 14 with 4-mercaptophenol 15 should produce the carboxylic acid 16 which may be converted to methyl ester 17. Alkylation with a halide or sulfonate 18 followed by saponification can then afford the phenylether 20.

Alternatively, intermediate 20 can be generated from the lactone derivative 5, 13 or 14 starting with bis(4-hydroxyphenyl)disulfide. Bis-alkylation with a halide or sulfonate 18 may produce the bis-phenylether 22. Reduction of the disulfide 22 using zinc should then yield thiophenol 23 which may then be reacted with the lactone 5, 13 or 14 to afford phenylether 20.

Scheme 4

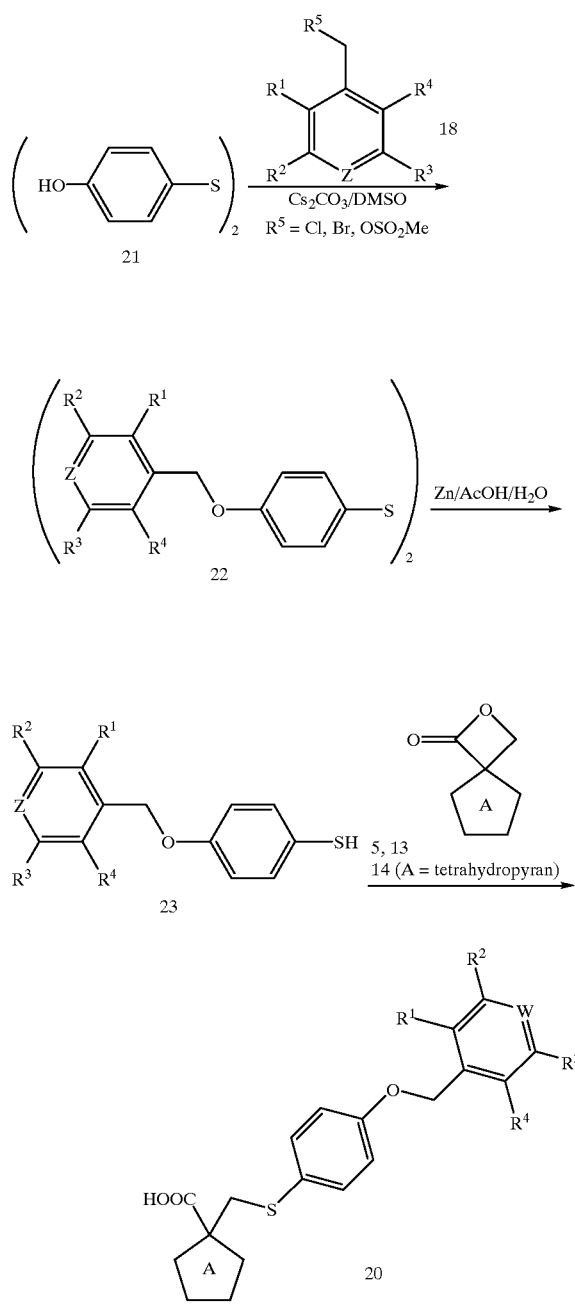

Conversion of 20 to a hydroxamic acid 24 can be accomplished by coupling with hydroxylamine hydrochloride using BOP (Scheme 5). Oxidation using oxone should produce the desired sulfone 25.

Scheme 5

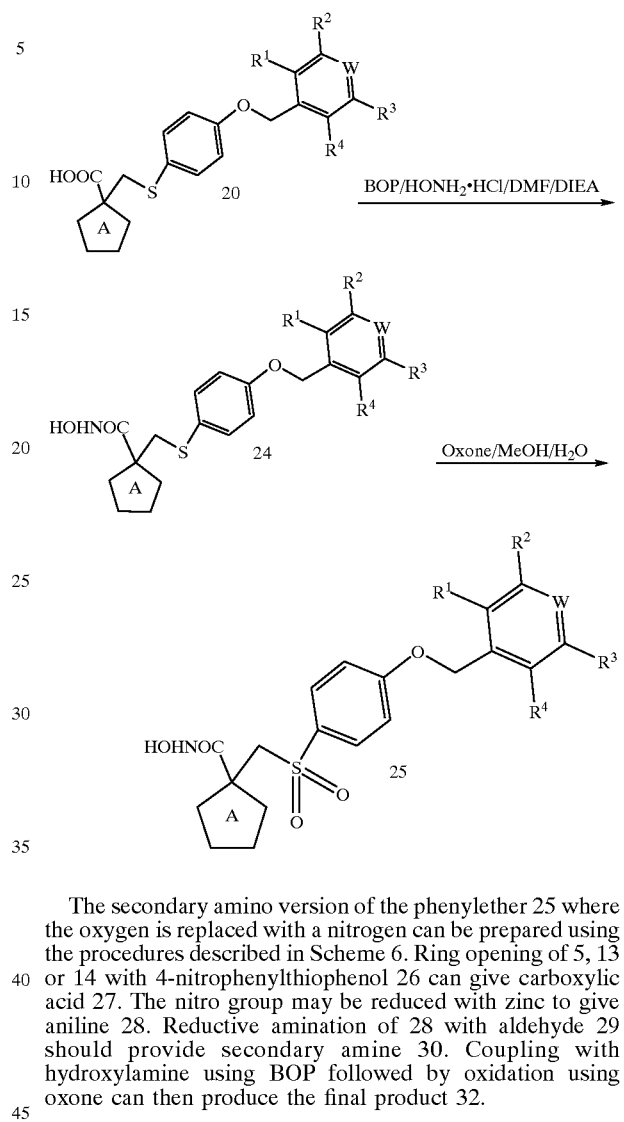

The secondary amino version of the phenylether 25 where the oxygen is replaced with a nitrogen can be prepared using the procedures described in Scheme 6. Ring opening of 5, 13 or 14 with 4-nitrophenylthiophenol 26 can give carboxylic acid 27. The nitro group may be reduced with zinc to give aniline 28. Reductive amination of 28 with aldehyde 29 should provide secondary amine 30. Coupling with hydroxylamine using BOP followed by oxidation using oxone can then produce the final product 32.

Scheme 6

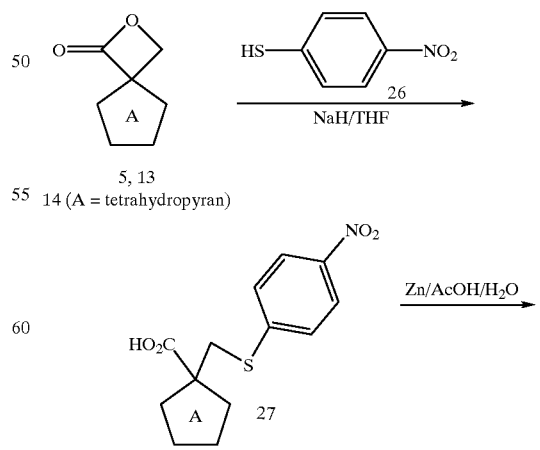

-continued

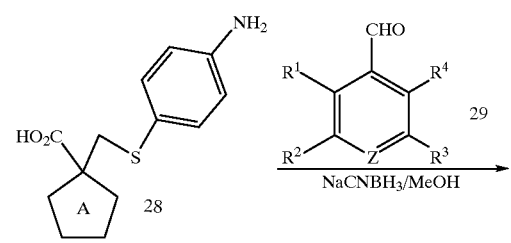

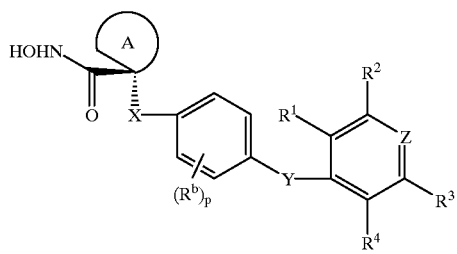

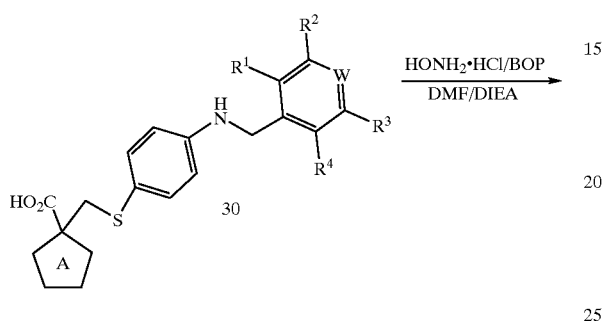

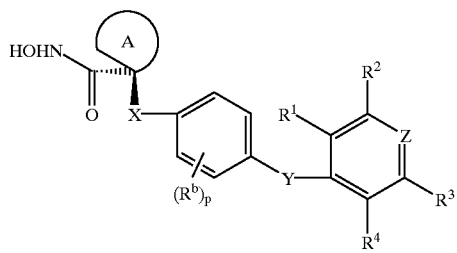

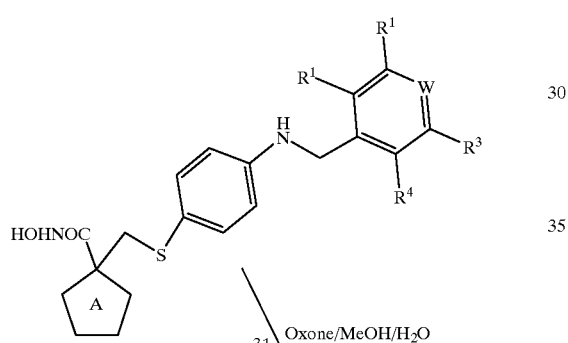

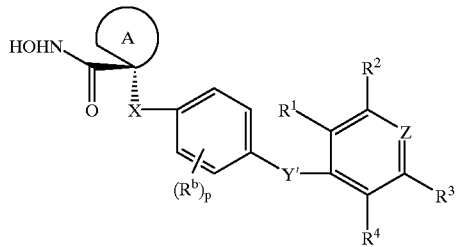

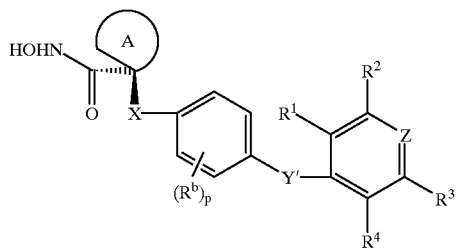

One diastereomer of a compound of Formula I may display superior activity compared with the others. Thus, formulae $I_1$, $I_2$, $II_1$, and $II_2$ are all considered part of the present invention.

When required, separation of the racemic material can be achieved by HPLC using a chiral column or by a resolution using a resolving agent such as camphonic chloride as in Steven D. Young, et al, *Antimicrobial Agents and Chemotheraphy,* 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C."

for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

4-[[[4-[(2,6-Dimethyl-4-pyridinyl)methoxy]phenyl]sulfonyl]methyl]tetrahydro-N -hydroxy-2H-pyran-4-carboxamide Mono(trifluoroacetate)

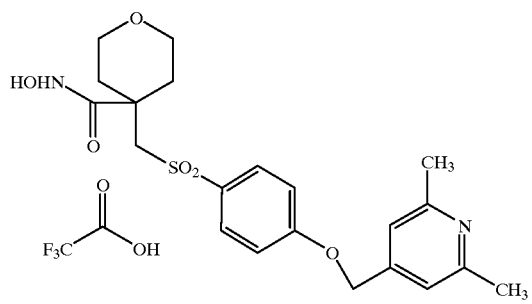

(1a) To a solution of 4-mercaptophenol (1.33 g, 10.6 mmol) in THF (30 mL) cooled in an ice bath was added NaH (0.98 g, 24.6 mmol). The mixture was allowed to warm to room temperature, stirred for 30 minutes and recooled to 0° C. To it was slowly added a solution of 2,7-dioxaspiro[3,5]nonane-1-one (1.0 g, 7 mmol) in THF (5 mL). The mixture was stirred at room temperature for 3 hours, quenched with 1 N HCl, and extracted with ethyl acetate. The organic layers were combined, washed with brine, dried (MgSO$_4$) and concentrated to give the carboxylic acid (1.14 g, 60%). MS(ESI): (M+H)$^+$=270.

(1b) To a solution of the acid (1a) (700 mg, 2.6 mmol) and 4-dimethylaminopyridine (63 mg, 0.5 mmol) in methylene chloride (5 mL) and methanol (1 mL) cooled in an ice bath was added 1,3-dicyclohexylcarbodiimide (640 mg, 3.1 mmol). The mixture was stirred at room temperature overnight. Insoluble material was filtered off and the solution was concentrated. Chromatography eluting with 50% ethyl acetate/hexane gave the methyl ester (410 mg, 57%). MS(ESI): (M+H)$^+$=284.

(1c) A mixture of the methyl ester (1b) (300 mg, 1.06 mmol), 2,6-dimethyl-4-picolyl chloride (213 mg, 1.3 mmol), cesium carbonate (1.03 g, 3.18 mmol) and tetrabutylamonium iodide (392 mg, 1.06 mmol) in DMSO (3 mL) was heated at 50° C. with stirring for 3 hours. Ethyl acetate was added and the solution was washed with brine, dried (MgSO$_4$) and concentrated. Chromatography on a reversed HPLC gave the phenylether as a TFA salt (235 mg, 46%) MS.(ESI): (M+H)$^+$=402.

(1d) A solution of the phenylether (1c) (200 mg, 0.388 mmol) in methanol (5 mL) and 1 N LiOH (4 mL) was refluxed for 5 hours. The solution was acidified with 1 N HCl and concentrated. The crude product was used for the next reaction without purification.

(1e) To a mixture of the crude acid (1d) (0.388 mmol), hydroxylamine hydrochloride (139 mg, 2 mmol) and diisopropylethylamine (0.7 mL, 4 mmol) in DMF (3 mL) cooled in an ice bath was added BOP (220 mg, 0.5 mmol). The mixture was stirred at room temperature for 2 hours and concentrated. Purification on HPLC gave the hydroxamic acid (95 mg, 49%). MS(ESI): (M+H)$^+$=403.2.

(1f) To a solution of the phenylether (1e) (95 mg, 0.23 mmol) in methanol (3 mL) cooled in an ice bath was added a solution of oxone (0.28 g, 0.46 mmol) in water (1 mL). The mixture was stirred at room temperature for 4 hours. Insoluble material was filtered off and the the solution was concentrated. Purification on reversed HPLC gave the sulfone (11 mg, 11%). MS(ESI): (M+H)$^+$=435.2.

Example 2

Tetrahydro-N-hydroxy-4-[[[4-(4-quinolinylmethoxy)phenyl]sulfonyl]methyl]-2H-pyran-4-carboxamide Mono(trifluoroacetate)

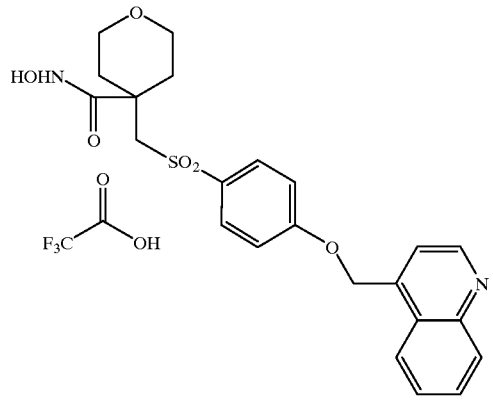

This compound was prepared using procedures analogous to those described in example 1 with the substitution of 4-chloromethylquinoline for 2,6-dimethyl-4-picolyl chloride. MS (ESI): (M+H)$^+$=457.2.

The following tables contain representative examples of the present invention. Each entry in each table is intended to be paired with each formula at the start of the table. For example, in Table 1, example 1 is intended to be paired with each of formulae a–o.

TABLE 1

Structures a, b-h, i-o shown with core scaffolds:

- a: tetrahydropyran core with CH₂-SO₂-C₆H₄-O- linker and C(O)NHOH
- b, Rᵃ = CH₃
- c, Rᵃ = CH₂CH₃
- d, Rᵃ = CH(CH₃)₂
- e, Rᵃ = cyclopropyl
- f, Rᵃ = cyclopentyl
- g, Rᵃ = benzyl
- h, Rᵃ = -CH₂-(4-pyridyl)

- i, Rᵃ' = CH₃
- j, Rᵃ' = CH₂CH₃
- k, Rᵃ' = CH(CH₃)₂
- l, Rᵃ' = cyclopropyl
- m, Rᵃ' = cyclopentyl
- n, Rᵃ' = benzyl
- o, Rᵃ' = -CH₂-(4-pyridyl)

Cores A, B, C, D:
- A: pyridine with $R^2$ and $R^3$
- B: quinoline with $R^2$
- C: 1,8-naphthyridine with $R^2$
- D: 1,7-naphthyridine with $R^1$

| Ex # | Core | $R^2$ | $R^3$ |
|---|---|---|---|
| 1 | A | CH₃ | CH₃ |
| 2 | A | OCH₃ | OCH₃ |
| 3 | A | OCH₂CH₃ | OCH₂CH₃ |
| 4 | A | OCH(CH₃)₂ | OCH(CH₃)₂ |
| 5 | A | Cl | Cl |
| 6 | B | H | — |
| 7 | B | CH₃ | — |
| 8 | B | OCH₃ | — |
| 9 | B | OCH₂CH₃ | — |
| 10 | B | OCH(CH₃)₂ | — |
| 11 | B | Cl | — |
| 12 | B | CH₂CH₃ | — |
| 13 | C | H | — |
| 14 | C | CH₃ | — |
| 15 | C | OCH₃ | — |
| 16 | C | OCH₂CH₃ | — |
| 17 | C | OCH(CH₃)₂ | — |
| 18 | C | Cl | — |
| 19 | C | CH₂CH₃ | — |
| 20 | D | H | |
| 21 | D | CH₃ | |
| 22 | D | OCH₃ | |
| 23 | D | OCH₂CH₃ | |
| 24 | D | OCH(CH₃)₂ | |
| 25 | D | Cl | |
| 26 | D | CH₂CH₃ | |

TABLE 2

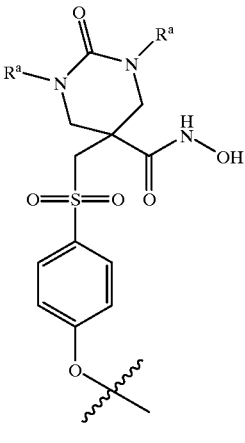

a, $R^a$ = $CH_3$
b, $R^a$ = $CH_2CH_3$
c, $R^a$ = $CH(CH_3)_2$
d, $R^a$ = cyclopropyl
e, $R^a$ = cyclopentyl
f, $R^a$ = benzyl h, $R^{a'}$ = $CH_3$
i, $R^{a'}$ = $CH_2CH_3$
j, $R^{a'}$ = $CH(CH_3)_2$
k, $R^{a'}$ = cyclopropyl
l, $R^{a'}$ = cyclopentyl
m, $R^{a'}$ = benzyl o, $R^{a'}$ = $CH_3$
p, $R^{a'}$ = $CH_2CH_3$
q, $R^{a'}$ = $CH(CH_3)_2$
r, $R^{a'}$ = cyclopropyl
s, $R^{a'}$ = cyclopentyl
t, $R^{a'}$ = benzyl g, $R^a$ = 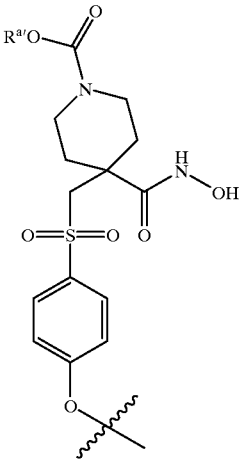

n, $R^a$ = 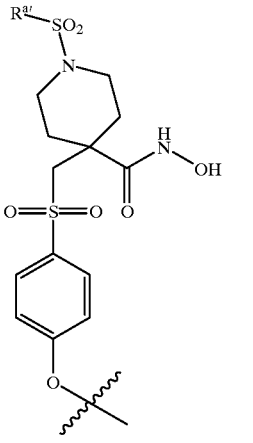

u, $R^{a'}$ = 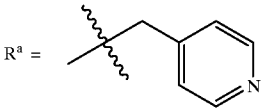

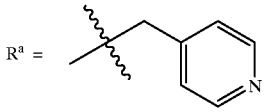
A

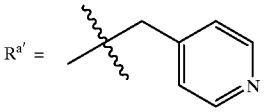
B

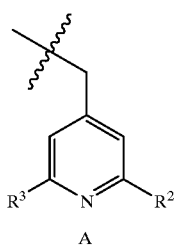
C

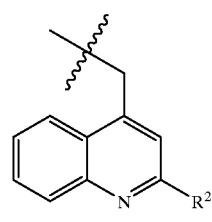
D

| Ex # | Core | $R^2$ | $R^3$ |
|------|------|-------|-------|
| 1 | A | $CH_3$ | $CH_3$ |
| 2 | A | $OCH_3$ | $OCH_3$ |
| 3 | A | $OCH_2CH_3$ | $OCH_2CH_3$ |
| 4 | A | $OCH(CH_3)_2$ | $OCH(CH_3)_2$ |
| 5 | A | Cl | Cl |
| 6 | B | H | — |
| 7 | B | $CH_3$ | — |
| 8 | B | $OCH_3$ | — |
| 9 | B | $OCH_2CH_3$ | — |
| 10 | B | $OCH(CH_3)_2$ | — |
| 11 | B | Cl | — |
| 12 | B | $CH_2CH_3$ | — |

TABLE 2-continued

| | | | |
|---|---|---|---|
| 13 | C | H | — |
| 14 | C | CH₃ | — |
| 15 | C | OCH₃ | — |
| 16 | C | OCH₂CH₃ | — |
| 17 | C | OCH(CH₃)₂ | — |
| 18 | C | Cl | — |
| 19 | C | CH₂CH₃ | — |
| 20 | D | H | — |
| 21 | D | CH₃ | — |
| 22 | D | OCH₃ | — |
| 23 | D | OCH₂CH₃ | — |
| 24 | D | OCH(CH₃)₂ | — |
| 25 | D | Cl | — |
| 26 | D | CH₂CH₃ | — |

TABLE 3

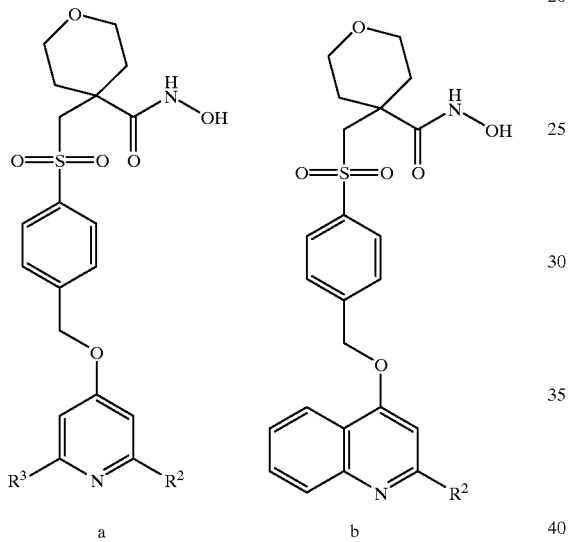

| Ex # | formula | R² | R³ |
|---|---|---|---|
| 1 | a | CH₃ | CH₃ |
| 2 | a | OCH₃ | OCH₃ |
| 3 | a | CF₃ | CF₃ |
| 4 | a | OCH₂CH₃ | OCH₂CH₃ |
| 5 | a | OCH(CH₃)₂ | OCH(CH₃)₂ |
| 6 | a | Cl | Cl |
| 7 | a | Br | Br |
| 8 | a | CH₃ | CH₃ |
| 9 | a | OCH₃ | OCH₃ |
| 10 | a | OCH₂CH₃ | OCH₂CH₃ |
| 11 | a | OCH(CH₃)₂ | OCH(CH₃)₂ |
| 12 | b | H | |
| 13 | b | CH₃ | |
| 14 | b | OCH₃ | |
| 15 | b | OCH₂CH₃ | |
| 16 | b | OCH(CH₃)₂ | |
| 17 | b | Cl | |
| 18 | b | CH₂CH₃ | |

TABLE 5

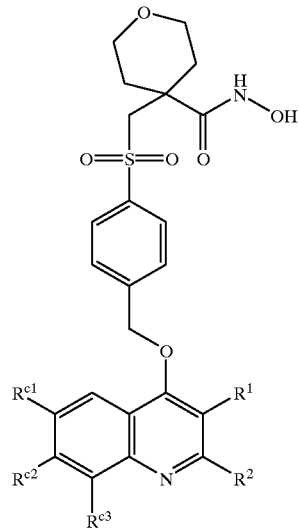

| Ex # | R² | R^{c1} | R^{c2} | R^{c3} | R¹ |
|---|---|---|---|---|---|
| 1 | CH₃ | H | H | H | H |
| 2 | H | H | H | H | H |
| 3 | H | H | Cl | H | H |
| 4 | H | H | CF₃ | H | H |
| 5 | H | OCH₃ | H | H | H |
| 6 | CH₃ | H | Cl | H | H |
| 7 | CH₃ | F | H | H | H |
| 8 | NH₂ | H | H | H | H |
| 9 | CF₃ | H | H | CF₃ | H |
| 10 | CH₃ | H | OCH₃ | H | H |
| 11 | CH₃ | H | H | CF₃ | H |
| 12 | CH₃ | H | CF₃ | H | H |
| 13 | CH₃ | H | H | CH₃ | H |
| 14 | CH₃ | Cl | H | Cl | H |
| 15 | CF₃ | H | Cl | H | H |
| 16 | H | H | H | CF₃ | H |
| 17 | CF₃ | H | Br | H | H |
| 18 | CF₃ | H | H | H | H |
| 19 | CF₃ | CH₃ | H | H | H |
| 20 | H | H | OCH₃ | H | H |
| 21 | CF₃ | H | H | OCF₃ | H |
| 22 | CF₃ | H | H | Br | H |
| 23 | H | CF₃ | H | H | H |
| 24 | CH₂CH₃ | H | H | H | H |
| 25 | CH(CH₃) | H | H | H | H |
| 26 | H | H | H | H | CH₃ |
| 27 | H | H | H | H | OCH₃ |
| 28 | H | H | H | H | Cl |

TABLE 6

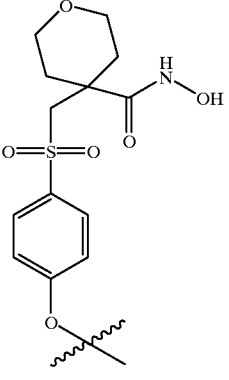

a b, R$^a$ = CH$_3$
c, R$^a$ = CH$_2$CH$_3$
d, R$^a$ = CH(CH$_3$)$_2$
e, R$^a$ = cyclopropyl
f, R$^a$ = cyclopentyl
g, R$^a$ = benzyl h, R$^a$ = 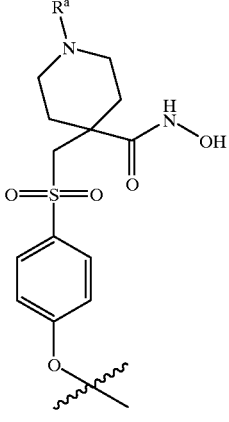

i, R$^{a'}$ = CH$_3$
j, R$^{a'}$ = CH$_2$CH$_3$
k, R$^{a'}$ = CH(CH$_3$)$_2$
l, R$^{a'}$ = cyclopropyl
m, R$^{a'}$ = cyclopentyl
n, R$^{a'}$ = benzyl o, R$^a$ = 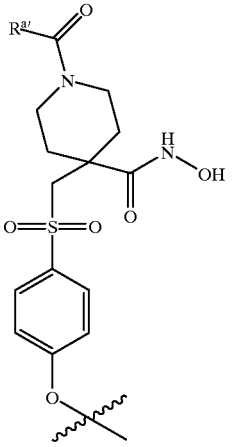

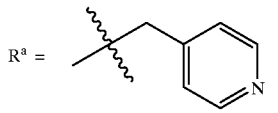

A

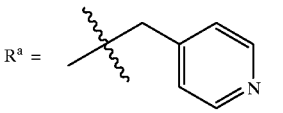

B

| Ex # | Core | R$^2$ | R$^3$ |
|---|---|---|---|
| 1 | A | CH$_3$ | CH$_3$ |
| 2 | A | OCH$_3$ | OCH$_3$ |
| 3 | A | CF$_3$ | CF$_3$ |
| 4 | A | OCH$_2$CH$_3$ | OCH$_2$CH$_3$ |
| 5 | A | OCH(CH$_3$)$_2$ | OCH(CH$_3$)$_2$ |
| 6 | A | Cl | Cl |
| 7 | A | Br | Br |
| 8 | B | CH$_3$ | — |
| 9 | B | CF$_3$ | — |
| 10 | B | Cl | — |

TABLE 7 a, R$^a$ = CH$_3$
b, R$^a$ = CH$_2$CH$_3$
c, R$^a$ = CH(CH$_3$)$_2$
d, R$^a$ = cyclopropyl
e, R$^a$ = cyclopentyl
f, R$^a$ = benzyl h, R$^{a'}$ = CH$_3$
i, R$^{a'}$ = CH$_2$CH$_3$
j, R$^{a'}$ = CH(CH$_3$)$_2$
k, R$^{a'}$ = cyclopropyl
l, R$^{a'}$ = cyclopentyl
m, R$^{a'}$ = benzyl o, R$^{a'}$ = CH$_3$
p, R$^{a'}$ = CH$_2$CH$_3$
q, R$^{a'}$ = CH(CH$_3$)$_2$
r, R$^{a'}$ = cyclopropyl
s, R$^{a'}$ = cyclopentyl
t, R$^{a'}$ = benzyl g, R$^a$ = (4-pyridylmethyl)

n, R$^{a'}$ = (4-pyridylmethyl)

u, R$^{a'}$ = (3-pyridylmethyl)

A

B

| Ex # | Core | R$^2$ | R$^3$ |
|---|---|---|---|
| 1 | A | CH$_3$ | CH$_3$ |
| 2 | A | OCH$_3$ | OCH$_3$ |
| 3 | A | CF$_3$ | CF$_3$ |
| 4 | A | OCH$_2$CH$_3$ | OCH$_2$CH$_3$ |
| 5 | A | OCH(CH$_3$)$_2$ | OCH(CH$_3$)$_2$ |
| 6 | A | Cl | Cl |
| 7 | A | Br | Br |
| 8 | B | CH$_3$ | — |
| 9 | B | CF$_3$ | — |
| 10 | B | Cl | — |

UTILITY

The compounds of formula I are expected to possess metalloproteinase and TNF inhibitory activity. The compounds provided by this invention should also be useful as standards and reagents in determining the ability of a potential pharmaceutical to inhibit MPs. These would be provided in commercial kits comprising a compound of this invention.

Compounds which inhibit the production or action of TNF and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, neurodejenerative diseases, and hyperoxic alveolar injury Some compounds of the present invention have been shown to inhibit TNF production in lipopolysacharride stimulated mice, for example, using the assay for TNF Induction in Mice and in cell assays as described below.

Some compounds of the present invention have been shown to inhibit aggrecanase a key enzyme in cartilage breakdown as determined by the aggrecanase assay described below.

As used herein "$\mu$pg" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of TNF-$\alpha$ production.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at 2×10 6 cells/ml in 96 well polystyrene plates. Cells were pro incubated 10 minutes with compound, then stimulated with 1 $\mu$g/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 $\mu$l of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 100 ng/ml LPS. Plates are incubated for 5 hours in an atmosphere of 5% $C_2$ in air. At the end of 5 hours, 750 $\mu$l of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50value.

TNF Induction In Mice

Test compounds are administered to mice either I.P. or P.O. at time zero. Immediately following compound administration, mice receive an I.P. injection of 20 mg of D-galactosainine plus 10 $\mu$g of lipopolysaccharide. One hour later, animals are anesthetized and bled by Cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Counterscreens

The enzymatic activities of recombinant MMP-1, 3 and 9 were measured at 25° C. with a fluorometric assay (Copeland, R. A.; Lombardo, D.; Giannaras, J. and Decicco, C. P. *Bioorganic Med. Chem. Lett.* 1995, 5 , 1947–1952). Final enzyme concentrations in the assay were between 0.05 and 10 nm depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the hydroxamic acids studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

Syrup

|  | Wt. % |
| --- | --- |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension

|  | Wt. % |
| --- | --- |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendable Powder

|  | Wt. % |
| --- | --- |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

|  | Wt. % |
| --- | --- |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

|  | Wt. % |
| --- | --- |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

|  | Wt. % |
| --- | --- |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed as new and desired to be secured by Letter Patent of United States is:

1. A compound of formula I:

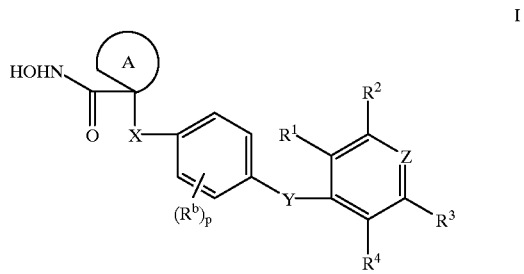

or a stereoisomer or pharmaceutically acceptable salt form thereof, wherein;

ring A is a 5–8 membered cyclic system containing 0–2 heteroatoms selected from the group: O, NH, S, SO, and $SO_2$, and substituted with 0–3 $R^a$;

$R^a$, at each occurrence, is independently selected from the group: =O, $CH_3$, $CH_2CH_3$, $CF_3$, Cl, F, OH, $OCH_3$, and $OCF_3$;

$R^b$, at each occurrence, is independently F or $CH_3$;

X is $CH_2S(O)_2$;

Y is $OCH_2$;

Z is N;

$R^1$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^2$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

$R^3$ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

provided that when Z is N, $R^2$ and $R^3$ are other than F, Br, or I;

$R^4$ is H;

alternatively, $R^3$ and $R^4$ are taken together with the carbon atoms to which they are attached to form a phenyl ring substituted with 0–2 $R^c$;

$R^c$ is selected from the group: H, F, Cl, Br, I, $NO_2$, $CH_3$, $CH_2CH_3$, $CH(CH_3)_2$, $OCH_3$, $OCH_2CH_3$, $OCH(CH_3)_2$, $CF_3$, and $OCF_3$;

when $R^3$ and $R^4$ are taken together, then $R^2$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;

n is selected from the group: 1, 2, and 3; and, p is selected from the group: 0, 1, and 2.

2. A compound according to claim 1, wherein the compound is of formula Ia:

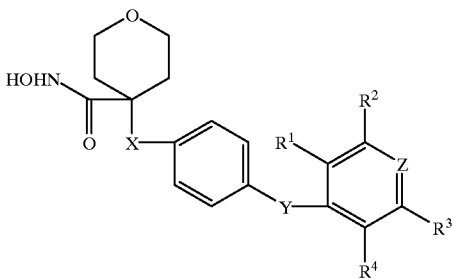

wherein,
R¹ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;
R² is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;
R³ is selected from the group: F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$;
R⁴ is H;
alternatively, R³ and R⁴ are taken together with the aromatic ring to which they are attached to form ring;

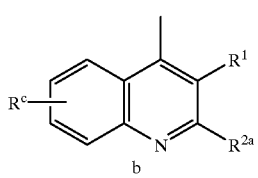

$R^c$ is selected from the group: H, F, Cl, Br, I, $NO_2$, $CH_3$, $CH_2CH_3$, $CH(CH_3)_2$, $OCH_3$, $OCH_2CH_3$, $OCH(CH_3)_2$, $CF_3$, and $OCF_3$; and,
$R^{2a}$ is selected from the group: H, F, Cl, Br, I, $CH_3$, $CH_2CH_3$, $CH(CH_3)_2$, $OCH_3$, $OCH_2CH_3$, $OCH(CH_3)_2$, $CF_3$, and $OCF_3$.

3. A compound according to claim 1, wherein the compound is selected from:
4-[[[4-[(2,6-dimethyl-4-pyridinyl)methoxy]phenyl]sulfonyl]methyl]-tetrahydro-N-hydroxy-2H-pyran-4-carboxamide;
Tetrahydro-N-hydroxy-4-[[[4-(4-quinolinylmethoxy)phenyl]sulfonyl]methyl]-2H-pyran-4-carboxamide;
Tetrahydro-N-hydroxy-4-[[[4-(5-quinolinylmethoxy)phenyl]sulfonyl]methyl]-2H-pyran-4-carboxamide;
N⁴-Hydroxy-4-[[[4-(4-quinolinylmethoxy)phenyl]sulfonyl]methyl]-4-piperidinecarboxamide;
N⁴-Hydroxy-4-[[[4-(5-guinolinylmethoxy)phenyl]sulfonyl]methyl]-4-piperidinecarboxamide;
1-Methanesulfonyl-4-[[[4-(4-quinolinylmethoxy)phenyl]sulfonyl]methyl]-N-hydroxy-4-piperidinecarboxamide;
1-Methanesulfonyl-4-[[[4-(5-quinolinylmethoxy)phenyl]sulfonyl]methyl]-N-hydroxy-4-piperidinecarboxamide;
11-Methoxycarbonyl-4-[[[4-(4-quinolinylmethoxy)phenyl]sulfonyl]methyl]-N-hydroxy-4-piperidinecarboxamide;
11-Methoxycarbonyl-4-[[[4-(5-quinolinylmethoxy)phenyl]sulfonyl]methyl]-N-hydroxy-4-piperidinecarboxamide;
11-Cyclopropanecarbonyl-4-[[[4-(4-quinolinylmethoxy)phenyl]sulfonyl]methyl]-N-hydroxy-4-piperidinecarboxamide;
11-Cyclopropanecarbonyl-4-[[[4-(5-quinolinylmethoxy)phenyl]sulfonyl]methyl]-N-hydroxy-4-piperidinecarboxamide;
11-Cyclopropyl-4-[[[4-(4-quinolinylmethoxy)phenyl]sulfonyl]methyl]-N-hydroxy-4-piperidinecarboxamide; and
11-Cyclopropyl-4-[[[4-(5-quinolinylmethoxy)phenyl]sulfonyl]methyl]-N-hydroxy-4-piperidinecarboxamide;
or a pharmaceutically acceptable salt form thereof.

4. A pharmaceutical composition, comprising: a pharmaceutically acceptable carrier and a therapeutically effective amount of a compound of claim 1 or a pharmaceutically acceptable salt form thereof.

5. A pharmaceutical composition, comprising: a pharmaceutically acceptable carrier and a therapeutically effective amount of a compound of claim 2 or a pharmaceutically acceptable salt form thereof.

6. A method for treating or preventing an inflammatory disorder, comprising: administering to a patient in need thereof a therapeutically effective amount of a compound of claim 1 or a pharmaceutically acceptable salt form thereof.

7. A method for treating or preventing an inflammatory disorder, comprising: administering to a patient in need thereof a therapeutically effective amount of a compound of claim 2 or a pharmaceutically acceptable salt form thereof.

8. A method of treating a condition or disease mediated by MMPs, TNF, aggrecanase, or a combination thereof in a mammal, comprising: administering to the mammal in need of such treatment a therapeutically effective amount of a compound of claim 1 or a pharmaceutically acceptable salt form thereof.

9. A method of treating a condition or disease mediated by MMPs, TNF, aggrecanase, or a combination thereof in a mammal, comprising: administering to the mammal in need of such treatment a therapeutically effective amount of a compound of claim 2 or a pharmaceutically acceptable salt form thereof.

10. A method of reducing levels of TNF in patients without inhibiting MMPs, comprising: MMP-1, MMP-2, and MMP-9, and reduce the potential of side effects mediated by these enzymes comprising: administering to the mammal in need of such treatment a therapeutically effective amount of a compound of claim 1 or a pharmaceutically acceptable salt form thereof.

11. A method of reducing levels of TNF in patients without inhibiting MMPs, comprising: MMP-1, MMP-2, and MMP-9, and reduce the potential of side effects mediated by these enzymes comprising: administering to the mammal in need of such treatment a therapeutically effective amount of a compound of claim 2 or a pharmaceutically acceptable salt form thereof.

12. A method of treating a condition or disease wherein the disease or condition is referred to as rheumatoid arthritis, osteoarthritis, periodontitis, gingivitis, corneal ulceration, multiple sclerosis, neurodegenerative diseases, psoriasis, autoimmune disease, Crohn's disease, inflammatory bowel disease, or HIV infection in a mammal, comprising: administering to the mammal in need of such treatment a therapeutically effective amount of a compound of claim 1 or a pharmaceutically acceptable salt form thereof.

13. A method of treating a condition or disease wherein the disease or condition is referred to as rheumatoid arthritis, osteoarthritis, periodontitis, gingivitis, corneal ulceration, multiple sclerosis, neurodegenerative diseases, psoriasis, autoimmune disease, Crohn's disease, inflammatory bowel disease, or HIV infection in a mammal, comprising: administering to the mammal in need of such treatment a therapeutically effective amount of a compound of claim 2 or a pharmaceutically acceptable salt form thereof.

14. A method of treating a condition or disease wherein the disease or condition is referred to as fever, cardiovascular effects, hemorrhage, coagulation, cachexia, anorexia, alcoholism, acute phase response, acute infection, shock, graft versus host reaction, solid tumor growth and tumor invasion by secondary metastases, or neovascular glaucoma, in a mammal comprising administering to the mammal in need of such treatment a therapeutically effective amount of a compound of claim 1 or a pharmaceutically acceptable salt form thereof.

15. A method of treating a condition or disease wherein the disease or condition is referred to as fever, cardiovascular effects, hemorrhage, coagulation, cachexia, anorexia, alcoholism, acute phase response, acute infection, shock, graft versus host reaction, solid tumor growth and tumor invasion by secondary metastases, or neovascular glaucoma, in a mammal comprising administering to the mammal in need of such treatment a therapeutically effective amount of a compound of claim 2 or a pharmaceutically acceptable salt form thereof.

16. A pharmaceutical composition, comprising: a pharmaceutically acceptable carrier and a therapeutically effective amount of a compound of claim 3 or a pharmaceutically acceptable salt form thereof.

17. A method for treating or preventing an inflammatory disorder, comprising: administering to a patient in need thereof a therapeutically effective amount of a compound of claim 3 or a pharmaceutically acceptable salt form thereof.

18. A method of treating a condition or disease mediated by MMPs, TNF, aggrecanase, or a combination thereof in a mammal, comprising: administering to the mammal in need of such treatment a therapeutically effective amount of a compound of claim 3 or a pharmaceutically acceptable salt form thereof.

19. A method of reducing levels of TNF in patients without inhibiting MMPs, comprising: MMP-1, MMP-2, and MMP-9, and reduce the potential of side effects mediated by these enzymes comprising: administering to the mammal in need of such treatment a therapeutically effective amount of a compound of claim 3 or a pharmaceutically acceptable salt form thereof.

20. A method of treating a condition or disease wherein the disease or condition is referred to as rheumatoid arthritis, osteoarthritis, periodontitis, gingivitis, corneal ulceration, multiple sclerosis, neurodegenerative diseases, psoriasis, autoimmune disease, Crohn's disease, inflammatory bowel disease, or HIV infection in a mammal, comprising: administering to the mammal in need of such treatment a therapeutically effective amount of a compound of claim 3 or a pharmaceutically acceptable salt form thereof.

21. A method of treating a condition or disease wherein the disease or condition is referred to as fever, cardiovascular effects, hemorrhage, coagulation, cachexia, anorexia, alcoholism, acute phase response, acute infection, shock, graft versus host reaction, solid tumor growth and tumor invasion by secondary metastases, or neovascular glaucoma, in a mammal comprising administering to the mammal in need of such treatment a therapeutically effective amount of a compound of claim 3 or a pharmaceutically acceptable salt form thereof.

22. A compound selected from the group:
Tetrahydro-N-hydroxy-4-[[[4-(5-isoquinolinylmethoxy) phenyl]sulfonyl]methyl]-2H-pyran-4-carboxamide;
$N^4$-Hydroxy-4-[[[4-(5-isoquinolinylmethoxy)phenyl] sulfonyl]methyl]-4-piperidinecarboxamide;
11-Methanesulfonyl-4-[[[4-(5-isoquinolinylmethoxy) phenyl]sulfonyl]methyl]-N-hydroxy-4-piperidinecarboxamide;
11-Methoxycarbonyl-4-[[[4-(5-isoquinolinylmethoxy) phenyl]sulfonyl]methyl]-N-hydroxy-4-piperidinecarboxamide;
11-Cyclopropanecarbonyl-4-[[[4-(5-isoquinolinylmethoxy) phenyl]sulfonyl]methyl]-N-hydroxy-4-piperidinecarboxamide; and,
11-Cyclopropyl-4-[[[4-(5-isoquinolinylmethoxy)phenyl] sulfonyl]methyl]-N-hydroxy-4-piperidinecarboxamide;
or a pharmaceutically acceptable salt form thereof.

23. A pharmaceutical composition, comprising: a pharmaceutically acceptable carrier and a therapeutically effective amount of a compound of claim 22 or a pharmaceutically acceptable salt form thereof.

24. A method for treating or preventing an inflammatory disorder, comprising: administering to a patient in need thereof a therapeutically effective amount of a compound of claim 22 or a pharmaceutically acceptable salt form thereof.

25. A method of treating a condition or disease mediated by MMPS, TNF, aggrecanase, or a combination thereof in a mammal, comprising: administering to the mammal in need of such treatment a therapeutically effective amount of a compound of claim 22 or a pharmaceutically acceptable salt form thereof.

26. A method of reducing levels of TNF in patients without inhibiting MMPs, comprising: MMP-1, MMP-2, and MMP-9, and reduce the potential of side effects mediated by these enzymes comprising: administering to the mammal in need of such treatment a therapeutically effective amount of a compound of claim 22 or a pharmaceutically acceptable salt form thereof.

27. A method of treating a condition or disease wherein the disease or condition is referred to as rheumatoid arthritis, osteoarthritis, periodontitis, gingivitis, corneal ulceration, multiple sclerosis, neurodegenerative diseases, psoriasis, autoimmune disease, Crohn's disease, inflammatory bowel disease, or HIV infection in a mammal, comprising: administering to the mammal in need of such treatment a therapeutically effective amount of a compound of claim 22 or a pharmaceutically acceptable salt form thereof.

28. A method of treating a condition or disease wherein the disease or condition is referred to as fever, cardiovascular effects, hemorrhage, coagulation, cachexia, anorexia, alcoholism, acute phase response, acute infection, shock, graft versus host reaction, solid tumor growth and tumor invasion by secondary metastases, or neovascular glaucoma, in a mammal comprising administering to the mammal in need of such treatment a therapeutically effective amount of a compound of claim 22 or a pharmaceutically acceptable salt form thereof.

* * * * *